United States Patent [19]
Allen

[11] Patent Number: 6,033,662
[45] Date of Patent: *Mar. 7, 2000

[54] OXYGEN ACTIVATABLE FORMULATIONS FOR DISINFECTION OR STERILIZATION

[75] Inventor: Robert C. Allen, San Antonio, Tex.

[73] Assignee: ExOxEmis, Inc., Little Rock, Ark.

[*] Notice: This patent is subject to a terminal disclaimer.

[21] Appl. No.: 09/056,541

[22] Filed: Apr. 7, 1998

Related U.S. Application Data

[60] Division of application No. 08/457,524, Jun. 1, 1995, Pat. No. 5,756,090, which is a continuation-in-part of application No. 08/343,781, Nov. 22, 1994, Pat. No. 5,451,402, which is a division of application No. 08/100,780, Aug. 2, 1993, Pat. No. 5,389,369, which is a continuation-in-part of application No. 07/660,994, Feb. 21, 1991, abandoned.

[51] Int. Cl.$^7$ ........................... C12N 9/08; A61K 37/50; A61K 31/195

[52] U.S. Cl. ........................... 424/94.4; 435/189; 435/190; 435/192; 422/28; 514/579; 514/42; 514/561; 514/564

[58] Field of Search ........................... 435/189, 190, 435/192; 424/94.4; 422/28; 514/579, 42, 561, 564

[56] References Cited

U.S. PATENT DOCUMENTS

| | | | |
|---|---|---|---|
| 2,679,533 | 5/1954 | Darragh et al. | 424/94.4 |
| 4,473,550 | 9/1984 | Rosenbaum et al. | 424/94.4 |
| 4,576,817 | 3/1986 | Montgomery et al. | 424/94.4 |
| 4,588,586 | 5/1986 | Kessler et al. | 424/94.4 |
| 4,726,948 | 2/1988 | Prieels et al. | 424/94.4 |
| 4,937,072 | 6/1990 | Kessler et al. | 424/94.4 |
| 4,996,146 | 2/1991 | Kessler | 435/28 |
| 5,108,899 | 4/1992 | Allen | 435/7.21 |
| 5,389,369 | 2/1995 | Allen | 424/94.4 |

FOREIGN PATENT DOCUMENTS

| | | |
|---|---|---|
| 30 098 073 | 1/1984 | European Pat. Off. |
| 0 307 376 | 3/1989 | European Pat. Off. |
| 30 361 908 | 4/1990 | European Pat. Off. |
| 10 397 227 | 11/1990 | European Pat. Off. |
| 0 500 387 A2 | 8/1992 | European Pat. Off. |
| 2 108 387 | 5/1983 | United Kingdom . |
| WO88/02600 | 4/1988 | WIPO . |
| WO89/12457 | 12/1989 | WIPO . |
| WO 91/06639 | 5/1991 | WIPO . |
| WO 91/11105 | 8/1991 | WIPO . |
| WO92/14484 | 9/1992 | WIPO . |
| WO95/04135 | 2/1995 | WIPO . |

OTHER PUBLICATIONS

Klebanoff, "Myeloperoxidase–Halide–Hydrogen Peroxide Antibacterial System," *J. Bacteriol.*, 95:2131–2138 (1968).

Allen, R.C., Dissertation entitled "Studies on the Generation of Electronic Excitation States in Human Polymorphonuclear Leukocytes and their Participation in Microbicidal Activity," Jul., 1973.

Allen, R.C. et al., "Evidence for the Generation of an Electronic Excitation State(s) in Human Polymorphonuclear Leukocytes and its Participation in Bactericidal Activity," *Biochemical and Biophysical Research Communications*, 47(4):679–684 (1972).

Allen, R.C., "Halide Dependence of the Myeloperoxidase–mediated Antimicrobial System of the Polymorphonuclear Leukocyte in the Phenomenon of Electronic Excitation," *Biochemical and Biophysical Research Communications*, 63(3):675–683 (1975).

Allen, R.C., "The Role of pH in the Chemiluminescent Response of the Myeloperoxidase–Halide–HOOH Antimicrobial System," *Biochemical and Biophysical Research Communications*, 63(3):684–691 (1975).

(List continued on next page.)

*Primary Examiner*—Jean C. Witz
*Attorney, Agent, or Firm*—Christensen O'Connor Johnson & Kindness PLLC

[57] ABSTRACT

Methods and compositions are disclosed for producing air-activated, i.e., oxygen ($O_2$) activated, disinfectant-sterilent solutions. Solutions containing a haloperoxidase (i.e., a halide:hydrogen peroxide ($H_2O_2$) oxidoreductase, such as myeloperoxidase, eosinophil peroxidase or lactoperoxidase) plus a halide or combination of halides (i.e., chloride, bromide and/or iodide), an oxidase (i.e., a substrate:$O_2$ oxidoreductase) capable of generating $H_2O_2$, and a substrate specific for that oxidase, are separately prepared under aerobic conditions, but all of the component solutions are made anaerobic prior to final combination and mixing. The anaerobic formulations are dispensed into containers capable of maintaining the anaerobic condition (e.g., pressurized canisters). Dispensing the solution at the time of use exposes the formulation to air (i.e., $O_2$) which activates its disinfectant-sterilent properties. $O_2$ is the rate limiting component for oxidase generation of $H_2O_2$. Under aerobic conditions the oxidase catalyzes the oxidation of its substrate and the reduction of $O_2$ to generate $H_2O_2$. In turn, $H_2O_2$ serves as substrate for haloperoxidase which catalyzes the oxidation of halide to hypohalous acid. Hypohalous acid reacts with an additional $H_2O_2$ to generate singlet molecular oxygen ($^1O_2$). Hypohalous acid (e.g., hypochlorous acid) and especially $^1O_2$ are potent microbicidal agents. Both haloperoxidase generation of hypohalous acid and its reactive consumption to yield $^1O_2$ are dependent on the availability of $H_2O_2$. A high rate of $H_2O_2$ generation does not result in the accumulation of hypohalous acid, but instead results in a high rate of $^1O_2$ production. The microbicidal capacity and toxicity of $^1O_2$ are limited by the half-life of this metastable electronically excited reactant, and as such, disinfectant-sterilent activity is temporally defined by and confined to the dynamics of oxidant generation.

The disinfectant-sterilent activity of formulation requires air exposure and is dependent on the presence of the halide-haloperoxidase combination employed, the activity of the oxidase present, the availability of oxidase-specific substrate and the availability of $O_2$.

22 Claims, No Drawings

OTHER PUBLICATIONS

Allen, R.C. and L.D. Loose, "Phagocytic Activation of a Luminol–Dependent Chemiluminescence in Rabbit Alveolar and Peritoneal Macrophages," *Biochemical and Biophysical Research Communications*, 69(1):245–252 (1976).

Allen, R.C., "Evaluation of Serum Opsonic Capacity by Quantitating the Initial Chemiluminescent Response from Phagocytizing Polymorphonuclear Leukocytes," *Infection and Immunity*, 15(3):828–833 (1977).

Allen, R.C. et al., "Correlation of Metabolic and Chemiluminescent Responses of Granulocytes from Three Female Siblings with Chronic Granulomatous Disease," *Journal of Infectious Diseases*, 136(4):510–518 (1977).

Allen, R.C., "Reduced, radical, and excited state oxygen in leukocyte microbicidal activity," In J.T. Dingle, P.J. Jacques and I.H. Shaw [eds.]. *Lysosomes in Applied Biology and Therapeutics*, North–Holland Publishing Company, 1979, pp. 197–233.

Allen, R.C., "Chemiluminescence: An Approach to the Study of the Humoral–phagocyte Axis in Host Defense Against Infection," *In Liquid Scintillation Counting, Recent Applications and Development*, vol. II. Sample Preparation and Applications, Academic Press, Inc., 1980, pp. 377–393.

Allen, R.C., et al., "Role of Myeloperoxidase and Bacterial Metabolism in Chemiluminescence of Granulocytes from Patients with Chronic Granulomatous Disease," *Journal of Infectious Diseases*, 144(4):34–348 (1981).

Allen, R.C. et al., "Humoral–Phagocyte Axis of Immune Defense in Burn Patients," *Archives of Surgery*, 117:133–140 (1982).

Allen, R.C., "Direct Quantification of Phagocyte Activity in Whole Blood: A Chemiluminigenic Probe Approach," In E. Kaiser, F. Gabl, M.M. Muller and P.M. Bayer [eds.] *Proceedings of XI International Congress of Clinical Chemistry*, Vienna, 1981. Walter de Gruyter, Berlin, New York, 1982, pp. 1043–1058.

Allen, R.C., "Biochemiexcitation: Chemiluminescence and the Study of Biological Oxygenation Reactions," In W. Adam and G. Cilento [eds.] *Chemical and Biological Generation of Excited States*, Academic Press, Inc., New York, 1982, pp. 309–344.

Allen, R.C., "Chemiluminescence and the Study of Phagocyte Redox Metabolism," In F. Rossi and P. Patrisica [eds.] *Biochemistry and Function of Phagocytes*, Plenum Publishing Corporation, 1982, pp. 411–421.

Allen, R.C. and M.M. Lieberman, "Kinetic Analysis of Microbe Opsonification Based on Stimulated Polymorphonuclear Leukocyte Oxygenation Activity," *Infection and Immunity* 45(2):475–482 (1984).

Allen, R.C., "Phagocytic Leukocyte Oxygenation Activities and Chemiluminescence: A Kinetic Approach to Analysis," In Marlene A. DeLuca and William D. McElroy [eds.] *Methods in Enzymology*, vol. 133, Bioluminescence and Chemiluminescence, Academic Press Inc., 1986, pp. 449–493.

Allen, R.C., "Oxygen–Dependent Microbe Killing by Phagocyte Leukocytes: Spin Conservation and Reaction Rate," In W. Ando and Y. Moro–oka [eds.] The Role of Oxygen in Chemistry and Biochemistry Proceedings of an International Symposium on Activation of Dioxygen and Homogeneous Catalytic Oxidations, Tsukuba, Japan, Jul. 12–16, 1987, *Studies in Organic Chemistry*, vol. 33, pp. 425–434, 1988 Elsevier Science Publishers B.V., Amsterdam.

Steinbeck, M.J. and J.A. Roth, "Neutrophil Activation by Recombinant Cytokines," *Reviews of Infectious Diseases*, 11(4):549–568 (1989).

Malech, H.L. and J.I. Gallin, "Medical Intelligence, Neutrophils in Human Diseases", *New England Journal of Medicine*, 317(11):687–694 (1987).

Olsson, K. and P. Venge, "The Role of the Human Neutrophil in the Inflammatory Reaction," *Allergy*, 35:1–13 (1980).

Chenoweth, D.E., "Complement Mediators of Inflammation," In Gordon D. Ross [ed.] *Immunobiology of the Complement System, An Introduction for Research and Clinical Medicine*, pp. 63–86, Academic Press, 1986.

Fearon, D.T. and L.A. Collins, "Increased Expression of C3b Receptors on Polymorphonuclear Leukocytes Induced by Chemotatic Factors and By Purification Procedures," *J. Immunology* 130(1):370–175 (1983).

Fearon, D.T. and W.W. Wong, "Complement Ligand–Receptor Interactions that Mediate Biological Responses," *Ann. Rev. Immunol.* 1:243–271 (1983).

Kearns, D.R. and A.U. Khan, "Sensitized Photooxygenation Reactions and the Role of Singlet Oxygen," *Photochemistry and Photobiology*, 10:193–210 (1969).

Kanofsky, J.R., "Singlet Oxygen Production by Lactoperoxidase," *Journal of Biological Chemistry*, 258(10):5991–5993 (1983).

Lehrer, R.I., "Antifungal Effects of Peroxidase Systems," *J. Bacteriol.* 99(2):361–365 (1969).

Klebanoff, S.J. et al., "The Peroxidase–Thiocyanate–Hydrogen Peroxide Antimicrobial System," *Biochimica et Biophysica Acta*, 117:63–72 (1966).

Klebanoff, S.J., "Myeloperoxidase–Halide–Hydrogen Peroxide Antibacterial System," *J. Bacteriol.* 95(6):2131–2138 (1968).

Klebanoff, S.J., "Myeloperoxidase–mediated Antimicrobial Systems and their Role in Leukocyte Function," reprinted from *Biochemistry of the Phagocytic Process*, Julius Schultz ed., (North–Holland Publishing Company, 1970), reprinted.

Klebanoff, S.J. et al., "Toxic Effect of the Peroxidase–Hydrogen Peroxide–Halide Antimicrobial System of *Mycobacterium leprae,*" *Infect. and Immun.* 44(2):534–536 (1984).

Hamon, C.B. et al., "A Peroxidase–mediated, Streptococcus mitis–dependent antimicrobial system in saliva," *J. Exp. Med.* 137:438–450 (1973).

Belding, M.E. et al., "Peroxidase–Mediated Virucidal Systems," *Science* 167:195–196 (1970).

Steele, W.F. et al., "Antistreptococcal Activity of Lactoperoxidase," *J. Bacteriol.* 97(2):635–639 (1969).

Mickelson, M.N. "Effect of Lactoperoxidase and Thiocyanate on the Growth of *Streptococcus pyogenes* and *Streptococcus agalactiae* in a Chemically Defined Culture Medium," *J. gen. Microbiol.* 43:31–43 (1966).

Yanagita, T., "Biochemical Aspects on the Germination of Conidiospores of *Aspergillus niger,*" *Archiv. für Mikrobiologic.* 26:329–344 (1957).

Halvorson, H. et al., "Biochemistry of Spores of Aerobic Bacilli With Special Reference to Germination," *Bac. Rev.* 21:112–131 (1957).

Smith, A.G. et al., "Application of Cholesterol Oxidase in the Analysis of Steroids," *J. of Chrom.* 101:373–378 (1974).

Richmond, W., "Preparation and Properties of a Cholesterol Oxidase from Nocardia sp. and Its Application to the Enzymatic Assay of Total Cholesterol in Serum," *Clin. Chem.* 19/12:1350–1356 (1973).

Weete, J.D., "Review Article, Sterols of the Fungi: Distribution and Biosynthesis," *Physiochemistry* 12:1843–1864 (1973).

Darrell, J. et al., "Lipid Metabolism of Fungal Spores," In International Fungal Spore Symposium, 2d, Brigham Young University, 1974, John Wiley & Sons, Inc., pp. 178, 180, 1976.

Lingappa, B.R., et al., "Phenethyl Alcohol Induced Germination of Ascospores of Neurospora," *Arch. Mikrobiol.* 72:97–105 (1970).

Sussman, A.S. et al., "Activation of Neurospora Ascospores by Organic Solvents and Furans," *Mycologia* 51:237–247 (1959).

Clark et al., Biosis Abstract, "Peroxidase–H2O2–halide system: Cytotoxic effect on mammalian tumor cells," *Blood* 45(2):161–170 (1975).

Rosen, H. et al., Biological Abstract No. 65021608; "Formation of Singlet oxygen by the Myelo Peroxidase Mediated Anti Microbial System," *J. Biol. Chem.* 252(14):4803–4810 (1977).

Thomas, E.L. et al., Biological Abstract No. 82079537; "Oxidation of Chloride and thiocyanate by isolated leukocytes," *J. Biol. Chem.* 261(21):9694–9702 (1986).

Paul, B.B. et al., "Role of the Phagocyte in Host–Parasite Interactions," *Infection and Immunity* 2(4):414–418 (1970).

Strauss, R.R. et al., "Role of the Phagocyte in Host–Parasite Interactions XXII. $H_2O_2$–Dependent Decarboxylation and Deamination by Myeloperosidase and Its Relationship to Antimicrobial Activity," *Res.–Journal of Reticuloendothelial Society* 7:754–761 (1970).

Zgliczynski, J.M. et al., "Myeloperoxidase of Human Leukaemic Leucocytes," *European J. Biochem.* 4:540–547 (1968).

Hills, G.M., "Chemical Factors in the Germination of Spore–bearing Aerobes: Observations on the Influence of Species, Strain and Conditions of Growth," *J. Gen. Microbiol.* 4:38–47 (1950).

Klebanoff, S.J., "Antimicrobial Mechanisms in Neutrophilic Polymorphonuclear Leukocytes," *Seminars in Hematology* 12(2):117–142 (1975).

Kaplan, E.L. et al., "Studies of Polymorphonuclear Leukocytes From Patients With Chronic Granulomatous Disease of Childhood: Bactericidal Capacity for Streptococci," *Pediatrics* 41(3):591–599 (1968).

Klebanoff, S.J. and White, L.R., "Iodination Defect in the Leukocytes of a Patient With Chronic Granulomatous Disease of Childhood," *New Engl. J. Med.* 280(9):460–466 (1987).

Mandell, G.L., "Catalase, Superoxide Dismutase, and Virulence of *Staphylococcus Aureus*. In Vitro and In Vivo Studies With Emphasis on Staphylococcal–Leukocyte Interaction," *J. Clin. Invest.* 55:561–566 (1975).

OXYGEN ACTIVATABLE FORMULATIONS FOR DISINFECTION OR STERILIZATION

This application is a divisional of application Ser. No. 08/457,524 filed Jun. 1, 1995, now U.S. Pat. No. 5,756,090, which is a continuation-in-part of application Ser. No. 08/343,781 filed Nov. 22, 1994, now U.S. Pat. No. 5,451,402, which is a divisional of application Ser. No. 08/100,780 filed Aug. 2, 1993, now U.S. Pat. No. 5,389,369, which is a continuation-in-part of application Ser. No. 07/660,994 filed Feb. 21, 1991, now abandoned.

FIELD OF THE INVENTION

The present invention relates to methods and compositions for antisepsis, disinfection or sterilization. More particularly, the present invention relates to methods and compositions that remain inactive as packaged for storage, but become active on exposure to air as an antiseptic, disinfection or sterilent agent when dispensed for use.

BACKGROUND OF THE INVENTION

Antisepsis is defined as substantial reduction of microbial content whereas disinfection is the elimination of all life forms capable of causing disease. Practically, disinfection implies destruction of all viable microorganisms except spores. Sterilization means the complete elimination of all viable microorganisms including spores (Hospital Infections, 2nd Ed. (Bennett, J. V. and Brachinan, P. S. eds.), Little, Brown and Co., Boston, Mass.), pp. 238–241, 1986). The acceptable methods of sterilization in current use are autoclaving (steam under pressure), dry heat, and gas sterilization (e.g., ethylene oxide). Sterilization by soaking in antiseptics is typically incomplete and is indicated only in circumstances where the sterilization methods described above are not applicable.

There are limitations to all of the sterilization methods described above. Many materials and devices are destroyed by dry heat or steam sterilization. Gas sterilization typically requires prolonged contact, e.g., exposure for greater than an hour, and a post-sterilization period for dissipation of the gas from the treated material. Lensed instruments or porous items typically require 24 to 48 hours of exposure to air before use. On the other hand, sterilization with germicidal agents, such as gluteraldehyde (2%), formaldehyde (8%)-alcohol (70%), or hydrogen peroxide (6%), requires exposure times ranging from 6 to 18 hours. These germicidal agents are also highly toxic and are indiscriminant in their toxic effect. As such, these sterilents cannot be brought in direct contact with host tissue, and have limited utility as sterilants for biomedical devices, such as contact lenses, medical and surgical instruments, and for wound cleaning. For example, an antimicrobial agent used to disinfect or sterilize a contact lens must possess a number of unique characteristics. On one hand, it must be effective against microorganisms which may be dangerous to the eye. At the same time, it must be tolerated in the delicate ocular environment of the user, and also not damage the contact lens itself. A number of contact lens disinfecting and preserving solutions are known in the art. Typically such solutions employ either sorbic acid, thimerosal, chlorhexidine, a polyquaternary germicide, a synthetic antibiotic or a conventional quaternary germicide, such as benzalkonium chloride. However, these conventional antimicrobial agents have drawbacks that tend to restrict their use. For example, sorbic acid characteristically contains formaldehyde residues, thimerosal in some patients acts as an allergy sensitizer, and chlorhexidine is relatively toxic. Also, a problem exists in that soft contact lens materials have a tendency to bind and concentrate antimicrobial agents and other active ingredients commonly found in contact lens care solutions, in some cases to hazardous levels. For example, benzalkonium chloride is typically not used with soft contact lenses due to its tendency to be taken up into the lens matrix. In addition, many of the antimicrobial agents known to date are relatively ineffective against a number of fungi and yeasts which are problematic in the ocular environment.

U.S. Pat. No. 5,389,369 discloses an improved haloperoxidase-based system for killing bacteria, yeast or sporular microorganisms by contacting the microorganisms, in the presence of a peroxide and chloride or bromide, with a haloperoxidase and an antimicrobial activity enhancing -amino acid. Although compositions and methods of U.S. Pat. No. 5,389,369 have been found to be highly effective antimicrobials, the components must be separately stored and maintained in order to prevent haloperoxidase/peroxide interaction and depletion prior to dispensing for use.

Therefore, there exists a need for methods and compositions for disinfecting and/or sterilizing materials or devices, such as contact lenses, surgical instruments and other biomedical devices, which is effective against bacteria, fungi and yeasts, which is tolerable by the user, which does not damage the devices, and which is designed for ease and convenience of storage and use. Ideally, such disinfectant-sterilent compositions should be fast acting with minimal host toxicity and maximal germicidal action. The compositions should be easy to deliver, should not damage the material or device treated, and should not cause damage to host tissue on contact. Depending upon the strength of composition and the time interval of exposure, the compositions should produce antisepsis, disinfection or sterilization.

SUMMARY OF THE INVENTION

The present invention describes methods and compositions for producing air-activated, i.e., oxygen ($O_2$) activated, disinfectant-sterilent solutions. Solutions containing a haloperoxidase (i.e., a halide:hydrogen peroxide ($H_2O_2$) oxidoreductase, such as myeloperoxidase, eosinophil peroxidase or lactoperoxidase) plus a halide or combination of halides (i.e., chloride, bromide and/or iodide) in appropriate concentrations, an oxidase (i.e., a substrate:$O_2$ oxidoreductase) capable of generating $H_2O_2$, and a substrate specific for that oxidase, are separately prepared under aerobic conditions, but all of the component solutions are made anaerobic prior to final combination and mixing. The anaerobic formulations are dispensed into containers capable of maintaining the anaerobic condition (e.g., pressurized canisters). Dispensing the solution at the time of use exposes the formulation to air (i.e., $O_2$) which activates its disinfectant-sterilent properties. $O_2$ is the rate limiting component for oxidase generation of $H_2O_2$. Under aerobic conditions the oxidase catalyzes the oxidation of its substrate and the reduction of $O_2$ to generate $H_2O_2$. In turn, $H_2O_2$ serves as substrate for haloperoxidase which catalyzes the oxidation of halide to hypohalous acid. Hypohalous acid reacts with an additional $H_2O_2$ to generate singlet molecular oxygen ($^1O_2$). Hypohalous acid (e.g., hypochlorous acid) and especially $^1O_2$ are potent microbicidal agents. Both haloperoxidase generation of hypohalous acid and its reactive consumption to yield $^1O_2$ are dependent on the availability of $H_2O_2$. A high rate of $H_2O_2$ generation does not result in the accumulation of hypohalous acid, but instead results in a high rate of $^1O_2$ production. The microbicidal capacity and toxicity of $^1O_2$ are limited by the half-life of this metastable electronically excited reactant, and as such, disinfectant-sterilent activity is temporally defined by and confined to the dynamics of oxidant generation. Disinfectant-sterilent activity of a formulation requires air exposure and is dependent on the presence of the halide-haloperoxidase combination employed, the activity of the oxidase present, the availability of oxidase-specific substrate and the availability of $O_2$.

For these disinfectant-sterilent formulations, $O_2$ is the essential and limiting component for microbicidal action. The formulation must contain sufficient haloperoxidase to produce the desired microbicidal effect. However, the relative concentrations of oxidase and its substrate can be adjusted to produce a broad spectrum of microbicidal activities ranging from rapid, high intensity microbicidal action of short duration to slow and prolonged microbicidal plus sporicidal action. By increasing the oxidase and making the oxidase substrate concentration limiting, the formulation will rapidly convert substrate to $H_2O_2$ producing a highly potent but time-limited microbicidal action. Once the substrate is exhausted there is a cessation of oxidative activity. On the other hand, limiting the concentration of oxidase limits the rate of $H_2O_2$ generation and produces a slow but sustained microbicidal action. The concentration of oxidase limits the rate of $H_2O_2$ production, and the concentration of substrate limits the quantity and duration of $H_2O_2$ production.

Haloperoxidases have a very high microbicidal capacity and low host toxicity. These characteristics, combined with the ability to formulate the temporal dynamics of disinfectant-sterilent activity (i.e., the ability to regulate the time period or window of maximum microbicidal action) assure excellent chemical sterilent activity with minimum host toxicity. In the absence of substrates, haloperoxidases show no direct toxicity to mammalian cells. Haloperoxidase oxidation and oxygenation activities are functionally linked to the availability of $H_2O_2$. As such, materials or devices (e.g., endoscopy tube) sterilized by these haloperoxidase formulations can be brought in direct contact with host tissue immediately following sterilization.

DETAILED DESCRIPTION OF THE PREFERRED EMBODIMENT

In accordance with the present invention, methods are provided for killing or inhibiting the growth of microorganisms comprising the steps of:

(a) maintaining under substantially anaerobic conditions a microbicidal composition comprising a haloperoxidase, a halide, and a peroxide generating agent capable of generating peroxide upon exposure to oxygen;

(b) exposing the composition to oxygen to activate the microbicidal activity of the composition; and (c) contacting the microorganisms with the activated composition to kill or inhibit the growth of the microorganisms.

The components are preferably prepared, combined and stored anaerobically (i.e., in the relative absence of oxygen). The anaerobic formulation remains inactive until exposed to air at the time of application. Air exposure provides oxygen, the rate limiting component for microbicidal action, to activate the formulation to kill or inhibit the growth of the microorganisms.

In another aspect of the present invention, hermetically sealed containers or packages are provided that maintain under substantially anaerobic conditions a formulation comprising a haloperoxidase, a halide, and a peroxide generating agent capable of generating peroxide upon exposure to oxygen. Means are provided for releasing the formulation from the container or package, whereby the formulation is activated upon exposure to air to enable killing or inhibition of the growth of microorganisms.

As used herein, the term "anaerobic" or "substantially anaerobic" means in the absence of oxygen or substantially in the absence of oxygen. Preferably, compositions of the invention are maintained until dispensed for use under substantially anaerobic conditions having less than about 1000 parts per million (ppm) of oxygen, more preferably less than about 500 ppm of oxygen, and most preferably less than about 250 ppm of oxygen.

Haloperoxidases useful in the present invention are defined as halide:hydrogen peroxide oxidoreductases (e.g., EC No. 1.11.1.7 and EC No. 1.11.1.10 under the International Union of Biochemistry) for which halide is the electron donor or reductant and peroxide is the electron receiver or oxidant. Any haloperoxidase which catalyzes the halide dependent generation of singlet molecular oxygen from hydrogen peroxide may be used in the present invention. Suitable haloperoxidases include myeloperoxidase (MPO), eosinophil peroxidase (EPO), lactoperoxidase (LPO), chloroperoxidase (CPO), and derivatives thereof, with the presently preferred haloperoxidases being myeloperoxidase and eosinophil peroxidase. By "derivatives thereof" as used herein generally means chemically or functionally modified MPO, EPO, CPO, and LPO which are capable of specifically binding to target microorganisms or specific eukaryotic cell types and which retain haloperoxidase activity in the enhancement of the disproportionation of peroxide to form singlet molecular oxygen in the presence of a suitable halide, as described herein.

Suitable halides for use in the methods and compositions of the invention include bromide, chloride and/or iodide. The use, selection, and amount of halide employed in a particular application will depend upon various factors, such as the haloperoxidase used in the antiseptic composition, the desired antiseptic, disinfection or sterilization effect, and other factors. When the haloperoxidase is MPO or CPO, the halide may be bromide or chloride. The amount of chloride employed will preferably fall in the range of about 10 $\mu$mol chloride to about 150 $\mu$mol chloride per ml of solution to approximate physiological conditions. When the haloperoxidase is EPO or LPO, chloride is relatively ineffective as a cofactor, and accordingly, the preferred halide is bromide. When included in liquid compositions, the compositions of the invention may comprise from about 1 nmol bromide to about 50 $\mu$mol bromide per ml of liquid composition, more preferably from about 10 nmol bromide to about 10 $\mu$mol bromide per ml of liquid composition, and most preferably from about 100 nmol bromide to about 1 $\mu$mol bromide per ml of liquid composition.

In the presence of sufficient halide, $H_2O_2$ is the rate limiting substrate for haloperoxidase microbicidal action. Microbicidal activity is linked to haloperoxidase generation of hypohalous acid:

(1)

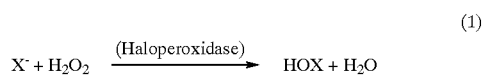

and to the secondary generation of singlet molecular oxygen ($^1O_2$):

$$HOX + H_2O_2 \rightarrow {}^1O_2 + X^- + H_2O \quad (2)$$

Both HOX and $^1O_2$ are potent antimicrobial reactants. Since $H_2O_2$ is required for HOX generation and $H_2O_2$ reacts with HOX to yield $^1O_2$, the haloperoxidase system guarantees that HOX generated will not accumulate but will further react to yield $^1O_2$, a metastable electronically excited molecule of potent reactivity but limited lifetime.

It is an important feature of the present invention that the haloperoxidase system components be maintained under anaerobic conditions until ready for use, and then be activated upon exposure to oxygen. This oxygen- or air-activated feature of the present invention results from including in the formulation an oxygen-dependent peroxide generating agent that produces peroxide on exposure to oxygen in the air. Suitable oxygen-dependent peroxide generating agents include any chemical system that can generate peroxide on exposure to $O_2$, provided the system does not inhibit haloperoxidase function, does not damage the materials or devices to be disinfected or sterilized, and is not toxic to mammalian tissue at the concentrations employed. In a presently particularly preferred embodiment, the peroxide generating agent comprises: (a) an oxidase (substrate:$O_2$ oxidoreductase), and (b) a substrate specific for the oxidase. Oxidases are substrate-specific enzymes that generate $H_2O_2$ on exposure to $O_2$, according to reaction (3):

$$\text{Substrate} + O_2 \xrightarrow{\text{Oxidase}} \text{Substrate}_{\text{Dehydrogenated}} + H_2O_2 \quad (3)$$

Since $H_2O_2$ production is dependent on both oxidase-specific substrate and $O_2$, oxidases are particularly useful in the practice of the invention. Representative oxidases for this purpose (together with their respective substrates) include, but are not limited to, glycollate oxidase, glucose oxidase, galactase oxidase, hexose oxidase, cholesterol oxidase, aryl-alcohol oxidase, L-gulonolacetone oxidase, galactose oxidase, pyranose oxidase, L-sorbose oxidase, pyridoxine oxidase, alcohol oxidase, L-2-hydroxyacid oxidase, ecdysome oxidase, choline oxidase, aldehyde oxidase, xanthine oxidase, pyruvate oxidase, oxalate oxidase, glyoxylate oxidase, pyruvate oxidase, D-aspartate oxidase, L-aminoacid oxidase, amine oxidase, pyridoxamine-phosphate oxidase, D-glutamate oxidase, ethanolamine oxidase, tyramine oxidase, putrascine oxidase, sarcosine oxidase, N-methylaminoacid oxidase, N-methyllysine oxidase, hydroxylnicotine oxidase, glycerol-3-phosphate oxidase, nitroethane oxidase, acetylindoxyl oxidase, urate oxidase, hydroxylamine amine oxidase, and sulphite oxidase. Oxidases that generate free radical hydrodioxylic acid ($HO_2$) and its conjugate base superoxide ($O_2^-$) can also be employed; ultimately these radical intermediates disproportionate to yield $H_2O_2$. When maintained under anaerobic conditions, the oxidase and its substrate are inactive because $O_2$ is unavailable to participate in the oxidase/substrate reaction (1). As such, no $H_2O_2$ is produced until the formulation is exposed to its rate limiting component, $O_2$.

Agents capable of producing hydrogen peroxide on exposure to oxygen, e.g., peroxide producing oxidases, are also particularly useful for dynamic control of the amounts of hydrogen peroxide present at the site of antimicrobial activity. Such agents maximize antimicrobial activity of the composition by providing and maintaining a steady, low level concentration of $H_2O_2$. Accordingly, the amount of such agents to be employed will be highly dependent on the nature of the agent and the effect desired, but will preferably be capable of producing a steady state level of from about 1 pmol to about 1 µmol of hydrogen peroxide per ml of liquid per minute, depending on the type and concentration of halide available at the site of antimicrobial activity. When the formulation is to be used as a disinfectant-sterilizing solution, the oxidase and its substrate can be adjusted to provide relatively high steady-state concentrations of $H_2O_2$ lasting for the required sterilization period. The disinfection-sterilizing action is terminated with exhaustion of the oxidase substrate or relative to the rate of oxidase degradation.

Optionally, the antimicrobial activity of the formulations of the invention against yeast and sporular microorganisms may be improved by including within the formualtions a suitable antimicrobial activity enhancing agent, as disclosed in U.S. Pat. No. 5,389,369, the disclosure of which is included herein by this reference. Generally, suitable antimicrobial activity enhancing agents of the invention are agents that enhance the antimicrobial activity of the haloperoxidase antimicrobial system against yeast and sporular microorganisms by labilizing the yeast and spore forms of microorganisms to haloperoxidase microbicidal activity, and that do not produce adverse effects on the haloperoxidase activity of the system or undesirable effects in the environment of use. Presently preferred activity enhancing agents of the invention include α-amino acid compounds of the formula:

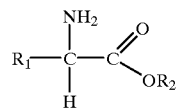

wherein $R_1$ is hydrogen, a straight or branched chain alkyl group having from 1 to 6 carbon atoms, or an unsubstituted or hydroxy or amino substituted straight or branched chain arylalky group having from 7 to 12 carbon atoms, and $R_2$ is hydrogen or a straight or branched chain alkyl group having from 1 to 6 carbon atoms. As used herein, amino acids may be in their acid form, as shown above, or may be in their zwitterionic form represented by the formula:

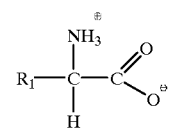

wherein $R_1$ and $R_2$ having the meanings set forth above, and may be in either l- or d-enantiomeric configurations. Representative alkyl $R_1$ groups include, for example, methyl, hydroxymethyl, isopropyl, 2-isobutyl, 1-isobutyl, hydroxy ethyl and amino butyl groups. Representative arylalkyl $R_1$ groups include, for example, tolyl and hydroxytolyl groups. Presently particularly preferred alkyl $R_2$ groups include methyl and ethyl groups. Representative antimicrobial activity enhancing agents of the invention include α-amino acids selected from the group consisting of glycine and the l- or d-enantiomers of alanine, valine, leucine, isoleucine, serine, threonine, lysine, phenylalanine, tyrosine and the alkyl esters thereof. The presently most preferred antimicrobial activity enhancing agents are glycine and l-alanine.

In accordance with other aspects of the invention, anaerobic formulations containing oxidase, oxidase-specific substrate, halide and haloperoxidase can be formulated and packaged for long-term storage at ambient temperature. Such formulations produce potent microbicidal action upon air exposure. Furthermore, $O_2$-activated disinfectant-sterilents can be formulated to achieve different degrees of potency and different temporal periods of activity. As can be deduced from equation (1), above, the rate of $H_2O_2$ generation is dependent on the concentration of oxidase, whereas the quantity of $H_2O_2$ generated is proportional to the quantity of substrate present. When substrate is not limiting, the rate of $H_2O_2$ generation is directly proportional to the oxidase activity. When oxidase activity is not limiting, the quantity and duration of $H_2O_2$ generation is dependent on the availability of oxidase-specific substrate. If a high potency, short lived disinfectant-sterilent action is desired, the formulation should have adequate haloperoxidase and halide, and a relatively high oxidase activity with substrate sufficient to confine activity to the desired time window. A lower potency but long-lived sterilent action can be formulated with adequate haloperoxidase and halide, relatively low oxidase activity, and sufficient substrate to sustain reaction for the temporal period desired. As shown in the following examples, systems of this type have been formulated to achieve sustained microbicidal-sporicidal action for a two-day period following air exposure.

In one particularly preferred embodiment, the methods and compositions of the invention are used as antiseptic agents exhibiting enhanced haloperoxidase antispore and antiyeast activity against a broad range of pathogenic microorganisms including bacteria and fungi. For use in contact with host tissue, the antiseptic systems are based on the use of dioxygenating haloperoxidase enzymes which exhibit selective affinity for pathogenic microorganisms. As such, high potency microbicidal action can be directed to the target microorganisms without associated host tissue destruction or disruption of normal flora; i.e., the antiseptic action is selective and confined to the target microorganism.

When properly formulated, haloperoxidase-enhancer preparations can be employed to disinfect and even sterilize materials and devices. High potency haloperoxidase-enhancer formulations can serve as in vitro disinfecting or sterilizing preparations. By limiting the time period of hydrogen peroxide availability, haloperoxidase-enhancer formulations can be made sufficiently potent to insure disinfection and even sterilization of a material or device before contact with host tissue. Any potential toxicity to normal flora and host tissue associated with the use of these high potency formulations will cease when peroxide is depleted, and as such, the formulation-treated material or device can be brought in contact with host tissue without additional washing to detoxification.

In another embodiment of the invention, the compositions of the invention may be specifically designed for in vitro applications, such as disinfecting or sterilization of medical devices, contact lenses and the like, particularly where the devices or lenses are intended to be used in contact with a patient or wearer. For applications of this type, the compositions may be conveniently provided in the form of a liquid or foam, and may be provided with emulsifiers, surfactants, buffering agents, wetting agents, preservatives, and other components commonly found in compositions of this type. Compositions of the invention may be impregnated into absorptive materials, such as sutures, bandages, and gauze, or coated onto the surface of solid phase materials, such as staples, zippers and catheters, which are packaged and maintained under substantially anaerobic conditions, such as in sealed foil and/or polymer pouches or bags that are impervious to air. The pouches or bags may then be opened to deliver the compositions to a site for the prevention of microbial infection. Other delivery systems of this type will be readily apparent to those skilled in the art.

Actual amounts of haloperoxidase, halide, peroxide generating agent and/or antimicrobial activity enhancing agents in the compositions of the invention may be varied so as to obtain amounts of haloperoxidase and antimicrobial activity enhancing agents at the site of treatment effective to kill vegetative microorganisms as well as yeast and sporular microorganisms. Accordingly, the selected amounts will depend on the nature and site for treatment, the desired response, the desired duration of microbicidal action and other factors. Generally, when the haloperoxidase is myeloperoxidase, eosinophil peroxidase, lactoperoxidase or compositions thereof, liquid compositions of the invention will comprise at least 0.01 picomoles (pmol) of haloperoxidase per ml of liquid composition, more preferably from about 0.1 pmol to about 500 pmol of haloperoxidase per ml of liquid composition, and most preferably from about 0.5 pmol to about 50 pmol of myeloperoxidase per ml of liquid composition. Optionally, it may be desirable in some applications to include both eosinophil peroxidase and myeloperoxidase in the same composition. Liquid compositions of the invention will generally further comprise from 100 μmol/ml to 300 μmol/ml chloride, from 10 μmol to 50 μmol/ml bromide, from 1 μmol/ml to 5 μmol/ml iodide, or combinations thereof Optionally, liquid compositions of the invention may generally comprise at least 0.005 μmol/ml of antimicrobial activity enhancing agents, i.e., -amino acids such as glycine and alanine, and more preferably from 0.05 μmol/ml to 50 μmol/ml of such antimicrobial activity enhancing agent. Finally, liquid compositions of the invention may generally comprise from 0.05 to 10 units/ml of an enzyme, such as glucose oxidase, capable of oxidizing a substrate, such as glucose, and reducing oxygen to hydroge peroxide; and may additionally comprise from 0.1 to 10 μmol/ml of a substrate for the enzyme. The foregoing components will typically be combined in a pharmaceutically acceptable liquid carrier.

As an illustrative example, a composition suitable for use as a contact lens solution may comprise from 1 to 20 pmol/ml of eosinophil peroxidase and/or myeloperoxidase, from 0.1 to 10 μmol/ml of glycine, from 0.01 to 10 units of glucose oxidase, and from 50 to 300 mEq/L of chloride with 0.1 to 5 mEq/L bromide. The above composition is combined with from 0.1 to 10 μmol/ml of glucose under anaerobic conditions and the complete preparation is kept anaerobic until used as a liquid disinfectant or sterilizing solution. Exposure to air, i.e., molecular oxygen, activates the disinfecting-sterilizing action of the formulation.

Due to the selective binding capacities of myeloperoxidase and eosinophil peroxidase, even relatively high potency formulations are of low toxicity to mammalian tissue. Furthermore, the ability to temporally limit the period of maximum potency further decreases the potential for host toxicity by confining the high potency disinfection-sterilization period to the time prior to host contact. As such, a material or device treated with the disinfectant-sterilent can be brought in direct contact with host tissue in the post sterilization period.

These and other aspects of the invention may be better understood in connection with the following examples, which are provided for purposes of illustration and not by way of limitation.

EXAMPLE 1

Anaerobic Formulation with Microbicidal Activity on Air Exposure

A gas tight glove box was prepared as an anaerobic chamber by first gassing with nitrogen ($N_2$, 99.99%

$O_2$-free). After the percentage of $O_2$ had fallen to 0.1%, 5 anaerobic gas packs were opened and activated in the chamber. The following solutions and bacterial suspension were prepared and placed in the anaerobic chamber:

($a_1$) Glucose Oxidase (GOX) prepared from Type VII *Aspergillus niger* GOX (Sigma Chemicals).

($a_2$) Acetate Buffer without GOX.

(b) Myeloperoxidase (MPO, Lot #1899201, ExOxEmis, Inc) solution containing D-glucose, chloride and a trace bromide.

(c) Suspension of *Staphylococcus aureus*.

Once the $O_2$ concentration had stabilized at between 0.01 and 0.02%, i.e., 100 to 200 parts per million (ppm), solution ($a_1$) or solution ($a_2$) was mixed with (b), and a portion of each mixture and a portion of the bacterial suspension (c) were removed from the chamber. After approximately ten minutes, the bacterial suspension was added to the aerobic and anaerobic mixtures with GOX ($a_1$) and without GOX ($a_2$). The final solutions contained either 0.6 units GOX or no GOX 56 micromoles ($\mu$mol) D-glucose, 5 picomoles (pmol) of MPO, and approximately $3 \times 10^7$ *Staphylococcus aureus* bacteria per ml of 50 mM acetate buffer with 100 mEq/l Cl$^-$ and 1 mEq/l Br$^-$, pH 6, in the presence and in the absence of air (ambient $O_2$). Samples (100 $\mu$l of mixed suspension) were removed from the test solutions at 1.25, 2.5, 5, 10 and 20 min and immediately diluted with 0.9 ml of 0.1% thioglycollate containing 200 units catalase (Sigma Chemicals) to terminate oxidative killing. The samples were further diluted and plated on trypticase soy agar (hockey stick technique). The bacterial colonies were counted after 1 to 2 days of incubation at 37° C., and *Staphylococcus aureus* survival is expressed as colony forming units (CFU) per ml of the original suspension as shown in Table 1. As used in Table 1 and the following examples, 0 indicates no growth at the lowest dilution tested; i.e., less than 100 CFU.

TABLE 1

Oxygen-Dependent Killing of *Staphylococcus aureus*

| Time in Min | *Staphylococcus aureus* (CFU/ml) | | | |
|---|---|---|---|---|
| | GOX (None) + MPO (5 pmol) | | GOX (0.6 unit) + MPO (5 pmol) | |
| | Anaerobic | Aerobic | Anaerobic | Aerobic |
| 1.25 | 31,000,000 | 28,400,000 | 24,400,000 | 0 |
| 2.5 | 25,200,000 | 26,200,000 | 24,800,000 | 0 |
| 5 | 29,600,000 | 26,000,000 | 25,600,000 | 0 |
| 10 | 26,000,000 | 39,400,000 | 900,000 | 0 |
| 20 | 22,000,000 | 27,400,000 | 760,000 | 0 |

Complete killing of *Staphylococcus aureus* was observed for the GOX-MPO complete system in the presence of $O_2$. Although no killing was observed from the GOX-MPO complete system in the absence of $O_2$ during the initial 5 min interval, incomplete killing was observed after 10 and 20 min exposure. This incomplete killing can be explained by the fact that the anaerobic chamber still contained 0.01 to 0.02% $O_2$. Although the $O_2$ concentration in the anaerobic chamber is about one-thousandth that of air, this quantity of $O_2$ is sufficient to produce a partial microbicidal action. No killing was observed with the MPO-only system (no GOX) in the presence or absence of $O_2$.

EXAMPLE 2

Anaerobic Preparation and $O_2$-Activation of Microbicidal-Sporicidal Activity of High Potency MPO- and EPO-Based Formulations The anaerobic chamber was prepared as described in Example 1, but the components comprising the GOX-XPO formulation were changed and glycine was added to facilitate sporicidal action, as described in Allen, U.S. Pat. No. 5,389,369. Two different formulations were anaerobically prepared. The first formulation contained 0.5 units GOX (Type VII *Aspergillus niger* GOX, Sigma Chemicals) plus 56 $\mu$mol D-glucose, 30 pmol MPO (porcine, Lot #1899201, ExOxEmis, Inc.) and 2 $\mu$mol glycine per ml of 50 mM acetate buffer with 100 mEq/l Cl$^-$ and 1 mEq/l Br$^-$, pH 6. The second formulation was the same but with 30 pmol EPO (Lot #1929201, ExOxEmis, Inc.) substituted for MPO. Both formulations were then allowed to age anaerobically for over a week before testing.

The microbicidal capacity of the GOX-MPO-glycine formulation was tested after 12 days of anaerobic storage. As indicated in Table 2, the formulation was tested against a broad range of gram negative and gram positive bacteria, yeast and fungal spores. Each test condition contained 400 $\mu$l of the GOX-MPO-glycine formulation and 200 $\mu$l of microbial suspension, and was activated by exposure to air (ambient $O_2$). Samples were removed after 0, 5, 10, and 20 min incubation (for the bacteria) and after 20, 30, 60 and 90 min incubation (for the yeast and fungal spores), and immediately diluted with 0.9 ml of 0.1% thioglycollate containing 200 units of catalase, diluted, and plated on trypticase soy agar (bacteria) or Sabouraud's dextrose agar (yeast and fungi). The colonies were counted after 1 to 4 days of incubation at 37° C.

The MPO concentration (18 pmol/ml, final) of this formulation effectively killed all gram negative and gram positive bacteria tested including Group A streptococcus. Killing was complete after 5 to 20 min exposure. The formulation also effectively killed the yeast and fungal spores tested, but a longer exposure, i.e., 30 to 90 min, was required for complete killing.

TABLE 2

Anaerobic Versus Aerobic Microbicidal Action of GOX-MPO-Glycine Formulation
0.3 units GOX, 18 pmol MPO & 1 $\mu$mol glycine
(final reaction conc. per ml)

| Time in Min | *Escherichia coli* | *Serratia marcesans* ATCC 14041 | *Pseudomonas aeruginosa* |
|---|---|---|---|
| 0 | 45,400,000 | 21,000,000 | 26,000,000 |
| 5 | 0 | 13,800,000 | 4,200,000 |
| 10 | 0 | 50,000 | 6,000 |
| 20 | 0 | 0 | 0 |

| | *Staphylococcus aureus* | *Streptococcus pyogenes* (Group A) | |
|---|---|---|---|
| 0 | 21,600,000 | 2,880,000 | |
| 5 | 60,000 | 0 | |
| 10 | 6,000 | 0 | |
| 20 | 0 | 0 | |

| | *Candida albicans* | *Aspergillus fumigatus* | *Fusarium moniliforme* |
|---|---|---|---|
| 0 | 1,100,000 | 100,000 | 88,000 |
| 20 | 420,000 | 280,000 | 54,000 |
| 30 | 166,000 | 0 | 4,400 |
| 60 | 0 | 0 | 800 |
| 90 | 0 | 0 | 0 |

The microbicidal capacity of the GOX-EPO-glycine formulation was tested after 13 days of anaerobic storage. This EPO-based formulation was tested against the same microbes under the same test conditions. The results are shown in Table 3.

This EPO-based formulation was as effective as the previously considered MPO-based formulation and was quicker acting. At this EPO concentration (18 pmol/ml, final) all gram negative and gram positive bacteria, including Group A streptococcus, were completely killed after 5 min exposure. Killing of Candida albicans and Fusarium moniliforme spores was also complete by 90 min.

TABLE 3

Anaerobic Versus Aerobic Microbicidal Action of
GOX-EPO-Glycine Formulation
0.3 units GOX, 18 pmol EPO & 1 μmol glycine
(final reaction conc. per ml)

| Time in Min | Escherichia coli | Serratia marcesans ATCC 14041 | Pseudomonas aeruginosa |
|---|---|---|---|
| 0 | 47,400,000 | 34,800,000 | 33,200,000 |
| 5 | 0 | 0 | 0 |
| 10 | 0 | 0 | 0 |
| 20 | 0 | 0 | 0 |

| | Staphylococcus aureus | Streptococcus pyogenes (Group A) |
|---|---|---|
| 0 | 19,200,000 | 1,000,000 |
| 5 | 0 | 0 |
| 10 | 0 | 0 |
| 20 | 0 | 0 |

| | Candida albicans | Fusarium moniliforme |
|---|---|---|
| 0 | 7,400,000 | 116,000 |
| 20 | 10,160 | 7,600 |
| 30 | 9,600 | 4,200 |
| 60 | 0 | 800 |
| 90 | 0 | 0 |

EXAMPLE 3

Preparation and Testing of $O_2$-Activated Microbicidal-Sporicidal Formulations Packaged Pressurized Spray Cans Preparation of Spray Sterilent Preparation of Stock Solutions: A 10% (volume/volume) Tween 80 solution prepared by adding 10 ml Tween 80 to 90 ml $H_2O$. A 1% (weight/volume) EDTA solution was prepared by adding 1 g $Na_2EDTA$ to 100 ml $H_2O$. A 0.1 M glycine solution was prepared by adding 1.5 g glycine (M.W. 75) to 200 ml $H_2O$. A 0.5% (w/v) hydroxypropyl-methyl-cellulose (HPMC, 100 centipoise) solution was prepared by adding 1 g HPMC to 200 ml $H_2O$ and gently mixing until fully dissolved. A 250 unit/ml GOX (Type VII from Aspergillus niger, Sigma Chemicals) was prepared in $H_2O$. A 0.1 M glucose solution was prepared by adding 1.8 g D-glucose (M.W. 180) to 100 ml $H_2O$.

Preparation of Simple Sterilent Working Stock:

| | Weight/Volume | Stock Solution | Final Concentration |
|---|---|---|---|
| (1.) | 5 ml | 10% Tween 80 | 0.1% |
| (2.) | 50 ml | 1% EDTA | 0.1% |
| (3.) | 10 ml | 0.1M Glycine | 2 mM |
| (4.) | 4 ml | 250 units/ml GOX | 2 units/ml |
| (5.) | 0.73 g | NaCl | 25 mM |
| (6.) | 0.05 g | NaBr | 1 mM |
| (7.) | 1.79 ml | MPOporcine | 50 pmol/ml |
| (8.) | uantum sufficit (qs) for 500 ml with Acetate Buffer, pH 5.5 (10 mM final) | | |

The ingredients described above were added to 300 ml $H_2O$ in the order indicated. Each stock addition was completely dissolved before the next addition. The working stock and D-glucose solutions were sterilized by passage through a 0.22 micron filter, and both solutions were placed in the anaerobic chamber. Once the chamber had stabilized at approximately 20 to 100 ppm $O_2$, 40 ml 0.1 M D-glucose were added to the working stock for a final concentration of 7 mM (130 mg/dL).

Approximately 100 ml of the complete Simple Sterilent Solution were added to 45×165 mm EP Spray System canisters (full capacity 140 ml) through a flap valve using an adapter-fitted syringe. The cans were then removed from the chamber and the outer compartment of the canister was pressurized with nitrogen gas ($N_2$).

| | Weight/Volume | Stock Solution | Final Concentration |
|---|---|---|---|
| (1.) | 5 ml | 10% Tween 80 | 0.1% |
| (2.) | 50 ml | 1% EDTA | 0.1% |
| (3.) | 50 ml | 0.5% HPMC | 0.05% |
| (4.) | 10 ml | 0.1 M Glycine | 2 mM |
| (5.) | 4 ml | 250 units/ml GOX | 2 units/ml |
| (6.) | 2.92 g | NaCl | 100 mM |
| (7.) | 0.05 g | NaBr | 1 mM |
| (8.) | 1.79 ml | $MPO_{porcine}$ | 50 pmol/ml |
| (9.) | qs for 500 ml with Acetate Buffer, pH 6 (10 mM final). | | |

The ingredients described above were added to 300 ml $H_2O$ in the order indicated. Each stock addition was completely dissolved before the next addition. The working stock and D-glucose solutions were sterilized by passage through a 0.22 micron filter, and both solutions were placed in the anaerobic chamber. Once the chamber had stabilized at approximately 20 to 30 ppm $O_2$, 40 ml 0.1 M D-glucose were added to the working stock for a final concentration of 7 mM (130 mg/dL). Approximately 100 ml of the complete Complex Sterilent Solution were added to each EP Spray System canister, and the canisters were pressurized with $N_2$ as previously described.

To test the microbicidal capacities of the Simple Sterilent Solution and the Complex Sterilent Solution against Escherichia coli and Aspergillus fumigatus (spores), 0.4 ml aliquots of freshly sprayed Simple Sterilent Solution (4 canisters tested) and Complex Sterilent Solution (3 canisters tested) were added to 0.1 ml of the microbe suspensions in the presence of air. A. fumigatus plates were read after 120 hrs incubation. The canister preparations were 16 days old at the time of testing. The results are presented in Table 4. Both sterilent solutions produced potent bactericidal action. Fungal sporicidal action was present but incomplete at 90 min exposure.

TABLE 4

Microbicidal Activity of the Simple and Complex Sterilent Solutions on Air Exposure

| Sterilent Solution Tested | Escherichia coli CFU/ml after 30 min | Aspergillus fumigatus CFU/ml after 90 min |
|---|---|---|
| Control | 175,600,000 | 940,000 |
| Simple | 0 | 46,000 |
| Simple | 0 | 32,000 |
| Simple | 0 | 60,000 |
| Simple | 0 | 40,000 |
| Complex | 0 | 800 |
| Complex | 0 | 56,000 |
| Complex | 0 | 44,000 |

The shelf life of the canisters of sterilent solution was tested by aging the preparations at 4° C., room temperature and 40° C. for approximately 1 month, and then repeating the procedure described above in connection with Table 4. The results are shown in Table 5.

TABLE 5

Effect of Temperature on the Microbicidal Capacity of the Simple and Complex Sterilent Solution Canisters

| Sterilent Solution Tested | Escherichia coli CFU/ml after 30 min | Aspergillus fumigatus CFU/ml after 90 min |
|---|---|---|
| Control | 48,000,000 | 1,020,000 |
| Simple | | |
| 4° C. | 0 | 220,000 |
| 23° C. | 0 | 220,000 |
| 40° C. | 0 | 180,000 |
| Complex | | |
| 4° C. | 0 | 260,000 |
| 23° C. | 0 | 220,000 |
| 40° C. | 0 | 200,000 |

As shown in Table 5, both the Simple Sterilent Solution and the Complex Sterilent Solution maintained full potency against *E. coli* after storage for 1 month. Fungicidal activity after the storage period against *A. fumigatus* was also observed.

EXAMPLE 4

Preparation, Luminescence-based Quality Control, and Microbicidal Capacity of a High Potency $O_2$-Activated Microbicidal-sporicidal Formulation Preparation of High Potency Working Stock

| | Weight/Volume | Stock Solution | Final Concentration |
|---|---|---|---|
| (1.) | 100 ml | 10% Tween 80 | 0.1% |
| (2.) | 1,000 ml | 1% EDTA | 0.1% |
| (3.) | 1,000 ml | 0.5% HPMC | 0.05% |
| (4.) | 200 ml | 0.1M Glycine | 2 mM |
| (5.) | 200 ml | 250 units/ml GOX | 5 units/ml |
| (6.) | 59.2 g | NaCl | 100 mM |
| (7.) | 1.0 g | NaBr | 1 mM |
| (8.) | 107.6 ml | $MPO_{porcine}$ | 150 pmol/ml |
| (9.) | qs for 10 liters with Acetate Buffer, pH 6.5 (10 mM final) | | |

The ingredients described above were mixed as described in Example 3. The working stock and a 0.56 M D-glucose solution were sterilized by passage through a 0.22 micron filter, and both solutions were placed in the anaerobic chamber. The large scale of this production made lowering and maintaining the $O_2$ concentration difficult. The minimum $O_2$ concentration achieved was 35 ppm. 125 ml 0.56 M D-glucose were added to the working stock for a final glucose concentration of 6.9 mM (130 mg/dL). Approximately 100 ml of the complete High Potency Sterilent Solution were added to each EP Spray System canister, and the canisters were pressurized with $N_2$ as described in Example 3. Ninety-nine canisters were filled.

The microbicidal capacities of early, middle and late production canisters were tested using the methodology previously described for the Table 4 data. *Escherichia coli* (119,800,000 CFU/test) were completely killed within 30 min by all of the canisters of sterilent tested. Although killing of *Aspergillus fumigatus* spores (2,300,000 CFU/test) was incomplete, the canisters of sterilent produced a hundredfold kill after 90 min exposure at room temperature.

EXAMPLE 5

Preparation and Testing of $O_2$-Activated Disinfectant-Sterilent Solutions Using Different Substrate-Oxidase Drivers Preparation of Lens Disinfectant-Sterilent Solution Preparation of Stock Solutions: Tween 80 and $Na_2EDTA$ solutions were prepared as described in Example 3. A 1.0 M glycine solution was prepared by adding 75 g glycine (M.W. 75) to 1 liter $H_2O$. A 1.0% (w/v) hydroxypropyl-methylcellulose (HPMC, 100 centipoise) solution was prepared by adding 5 g HPMC to 500 ml $H_2O$ and gently mixing until fully dissolved. Acetate Buffer (20 mM, pH 6.8) was prepared by adding 1.2 ml glacial acetic acid ($C_2H_4O_2$, M.W. 60) and 1.64 g of sodium acetate ($NaC_2H_3O_2$, M.W. 82) per liter of $H_2O$.

Preparation of Common Working Stock

| | Weight/Volume | Stock Solution | Final Concentration |
|---|---|---|---|
| (1.) | 0.2 liters | 10% Tween 80 | 0.1% |
| (2.) | 1.0 liters | 1% EDTA | 0.05% |
| (3.) | 2.0 liters | 1% HPMC | 0.1% |
| (4.) | 50 ml | 1.0M Glycine | 2.5 mM |
| (5.) | 171 g | NaCl | 145 mM |
| (6.) | 2.0 g | NaBr | 1 mM |
| (7.) | qs for 20 liters with Acetate Buffer (10 mM final). Adjust pH to 6.8 with HCl/NaOH as required prior to filtration. Estimated osmolality 310 mOsm; range of osmolality for tears is 309 to 347 mOsm. | | |

The ingredients were mixed as previously described. The working stock was used to prepare four different substrate-oxidase preparations. The four oxidases tested were: (1) choline oxidase, (2) glycerol-3-phosphate oxidase, (3) galactose oxidase, and (4) D-amino acid oxidase. The final oxidase activity of all of the preparations was 1 unit/ml of the final preparation. Choline, glycerol-3-phosphate, D-galactose and glycine were included at a final concentration of 2.5 mM as substrates for the oxidases. The MPO concentration of the preparation was approximately 100 pmol/ml. The solutions were sterilized by passage through a 0.22 micron filter and placed in the anaerobic chamber. The minimum $O_2$ concentration achieved was 10 ppm. After depletion of $O_2$, the oxidases and their specific substrates were added to the various preparations in the anaerobic chamber. Approximately 100 ml of each of the complete Substrate-Oxidase Sterilent Solutions were added to each EP Spray System canister, and the canisters were pressurized with $N_2$ as described in Example 3.

These experiments were designed to test the possibilities of using substrate-oxidase combinations other than glucose-glucose oxidase to formulate $O_2$-activated disinfectant-sterilent solutions. Using the procedure of Example 3, the antimicrobial activity of each preparation was tested against *E. coli* and *S. aureus*. The results of testing are presented in Table 6, in which "Dilution" indicates the dilution of the sterilent; i.e., the final ratio of MPO:Oxidase to microbe suspension, and 0 indicates no growth at the lowest dilution tested; i.e., less than 100 CFU.

TABLE 6

Microbicidal Capacities of Various Substrate-Oxidase Formulations

| Formulations, MPO: Oxidase Combinations: Dilution 1:1.1 | *Escherichia coli* CFU/ml after 30 min | *Staphylococcus aureus* CFU/ml after 30 min |
|---|---|---|
| Control | 6,400,000 | 9,400,000 |
| MPO:Choline Ox (1U) | 34,000 | 8,800,000 |
| MPO:Glycerol-3-P Ox (1U) | 110,000 | 1,110,000 |
| MPO:Galactose Ox (1U) | 0 | 0 |
| MPO:D-AA Ox (1U) | 22,000 | 0 |

Each of the substrate-oxidase formulations of Table 6 showed microbicidal action, but none of the preparations tested demonstrated any special advantage over the previously tested glucose-glucose oxidase system.

EXAMPLE 7

Preparation and Testing of $O_2$-Activated Disinfectant-Sterilent Formulations for Ophthalmic Use Preparation of Lens Disinfectant-Sterilent Solution Preparation of Stock Solutions: The stock solutions were essentially the same as described for Example 6.

Preparation of Lens Disinfectant-Sterilent Working Stock

| | Weight/Volume | Stock Solution | Final Concentration |
|---|---|---|---|
| (1.) | 190 ml | 10% Tween 80 | 0.1% |
| (2.) | 50 ml | 1% EDTA | 0.05% |
| (3.) | 100 ml | 1% HPMC | 0.1% |
| (4.) | 30 ml | 0.1M Glycine | 3.0 mM |
| (5.) | 8.76 g | NaCl | 150 mM |
| (6.) | 0.1 g | NaBr | 1 mM |
| (7.) | 30 ml | 0.1M D(+) Glucose | 3 mM |
| (8.) | qs for 1 liter with 20 mM Acetate Buffer. Adjust final pH to 6.8 with HCl/NaOH as required prior to filtration. Estimated osmolality 325 mOsm; the osmolality for tears is 309 to 347 mOsm. | | |

The ingredients were mixed as previously described to produce the working stock. The glucose oxidase Type VII (1,000 units GOX/mi) was added to the stock to prepare four formulations:

Formulation A: 0.5 ml GOX/liter solution∴0.5 units/ml (final).

Formulation B: 1 ml GOX/liter solution∴1 units/mil (final).

Formulation C: 2 ml GOX/liter solution∴2 units/ml (final).

Formulation D: 4 ml GOX/liter solution∴4 units/ml (final).

The MPO concentration of the preparation (undiluted) was approximately 100 pmol/ml. The solutions were sterilized by passage through a 0.22 micron filter and placed in the anaerobic chamber. The minimum $O_2$ concentration achieved was 10 ppm. After depletion of $O_2$, the oxidases and their specific substrates were added to the various preparations in the anaerobic chamber. Approximately 100 ml of each of the complete Lens Disinfectant-Sterilent Formulations were added to each EP Spray System canister, and the canisters were pressurized with $N_2$ as previously described.

These four preparations were designed and tested to achieve a contact lens care disinfectant-sterilent formulation with excellent microbicidal-sporicidal capacity and minimum potential for host toxicity. The experiments with these formulations were also designed to answer questions regarding duration of activity after exposure to $O_2$ and long range shelf stability of the canister preparations. The microbicidal-sporicidal activities of the formulations immediately, 2 hours and 4 hours after air exposure against *S. aureus*, *E. coli* and *A. fumigatus* were tested using the procedure of Example 3. The results are shown in Table 7. The formulations had been packaged in the canisters and stored for six months at the time of testing.

TABLE 7

Microbicidal Activity Relative to Period of Air Exposure for Ophthalmic Disinfectant-Sterilent Formulations (6 Months After Manufacture)

| Formulation Tested | Time, Post $O_2$ Exposure | CFU/ml after 1 Hour | | |
|---|---|---|---|---|
| | | *Staph. aureus* | *E. coli* | *A. fumigatus* |
| Control | Immediate | 285,200,000 | 221,600,000 | 5,500,000 |
| Control-MPO | Immediate | 263,000,000 | 101,600,000 | 5,360,000 |
| Formulation A | Immediate | 0 | 0 | 4,340,000 |
| Formulation B | Immediate | 0 | 0 | 760,000 |
| Formulation C | Immediate | 0 | 0 | 5,200 |
| Formulation D | Immediate | 0 | 0 | 400 |
| Formulation A | 2 Hours | 0 | 0 | 420,000 |
| Formulation B | 2 Hours | 0 | 0 | 5,800 |
| Formulation C | 2 Hours | 0 | 0 | 600 |
| Formulation D | 2 Hours | 0 | 0 | 200 |
| Formulation A | 4 Hours | 0 | 0 | 64,000 |
| Formulation B | 4 Hours | 0 | 0 | 6,200 |
| Formulation C | 4 Hours | 0 | 0 | 0 |
| Formulation D | 4 Hours | 0 | 0 | 0 |

Complete *Staphylococcus aureus* and *Escherichia coli* killing was observed for all of the formulations at all of the post-$O_2$ exposure times tested. Killing of *Aspergillus fumigatus* spores immediately after exposing the formulations to air was proportional to the GOX concentration of the formulations. Formulation A (0.5 units GOX/ml) produced only minimal killing. Formulations B, C and D with progressively higher GOX activities produced progressively greater killing. The formulations showed even better microbicidal-sporicidal activity at 2 hours and 4 hours post-$O_2$ exposure. In fact, the formulations were most effective at 4 hours post-$O_2$ exposure. In order to further investigate this trend, the experiment was extended to include longer post-$O_2$ exposure times, using formulations that had been stored in canisters for 7 months. The results of testing are presented in Table 8.

TABLE 8

Microbicidal Activity Relative to Period of Air Exposure for Ophthalmic Disinfectant-Sterilent Formulations (7 Months After Manufacture)

| Formulation Tested | Time, Post $O_2$ Exposure | CFU/ml after 1 Hour | | |
|---|---|---|---|---|
| | | Staph. aureus | E. coli | A. fumigatus |
| Control | 4 Hours | 97,000,000 | 323,200,000 | 6,420,000 |
| Control-MPO | 4 Hours | 81,600,000 | 296,800,000 | 3,160,000 |
| Formulation A | 4 Hours | 0 | 0 | 1,400,000 |
| Formulation B | 4 Hours | 0 | 0 | 1,200,000 |
| Formulation C | 4 Hours | 0 | 0 | 100,000 |
| Formulation D | 4 Hours | 0 | 0 | 1,600 |
| Formulation A | 8 Hours | 0 | 0 | 720,000 |
| Formulation B | 8 Hours | 0 | 0 | 600 |
| Formulation C | 8 Hours | 0 | 0 | 600 |
| Formulation D | 8 Hours | 0 | 0 | 0 |
| Formulation A | 12 Hours | 5,000 | 0 | 340,000 |
| Formulation B | 12 Hours | 0 | 0 | 27,000 |
| Formulation C | 12 Hours | 0 | 0 | 4,200 |
| Formulation D | 12 Hours | 0 | 0 | 2,200 |
| Formulation A | 24 Hours | 206,000 | 0 | 1,860,000 |
| Formulation B | 24 Hours | 0 | 0 | 98,000 |
| Formulation C | 24 Hours | 0 | 0 | 184,000 |
| Formulation D | 24 Hours | 0 | 0 | 9,400 |

The results for the 4-hour post-$O_2$ exposure testing are essentially in agreement for both the initial (Table 7) and follow-up experiment (Table 8). The microbicidal-sporicidal activities of the formulations at 8-hour post-$O_2$ exposure remain the same or slightly increased. However, at 12 hours and especially at 24 hours post-$O_2$ exposure, a small decrease in *Staphylococcus aureus* and *Aspergillus fumigatus* spore killing was noted.

As disclosed in U.S. Pat. No. 5,389,369, fungal spore killing requires a relatively long time period of exposure to MPO:GOX disinfectant-sterilent solutions. As such, the 12- and 24-hours post-$O_2$ exposure experiments of Table-8 were repeated, using formulations that had been stored in canisters for 8 months, to allow comparison of bactericidal-fungicidal action resulting from 1 hour and 4 hours exposure to the disinfectant-sterilent formulations. The results are presented in Table 9.

TABLE 9

Microbicidal Activity Relative to Period of Air Exposure and Period of Microbial Contact for the Ophthalmic Disinfectant-Sterilent Formulations (8 Months After Manufacture)

| Formulation Tested | Time, Post $O_2$ Exposure | CFU/ml | | |
|---|---|---|---|---|
| | | Staph. aureus | E. coli | A. fumigatus |
| | | Incubation Time, 1 Hour | | |
| Control | 12 Hours | 169,600,000 | 142,800,000 | 3,560,000 |
| Control-MPO | 12 Hours | 145,600,000 | 140,600,000 | 3,380,000 |
| Formulation A | 12 Hours | 4,200 | 0 | 1,200,000 |
| Formulation B | 12 Hours | 660,000 | 0 | 13,800 |
| Formulation C | 12 Hours | 0 | 0 | 3,600 |
| Formulation D | 12 Hours | 40,000 | 0 | 2,200 |
| | | Incubation Time, 4 Hours | | |
| Formulation A | 12 Hours | 0 | 0 | |
| Formulation B | 12 Hours | 0 | 0 | 0 |
| Formulation C | 12 Hours | 0 | 0 | 0 |
| Formulation D | 12 Hours | 0 | 0 | 0 |
| Formulation A | 24 Hours | 0 | 0 | 0 |
| Formulation B | 24 Hours | 0 | 0 | 0 |
| Formulation C | 24 Hours | 0 | 0 | 0 |
| Formulation D | 24 Hours | 0 | 0 | 0 |

The microbicidal capacities of the formulations, after storage in the canisters for 11 months, were tested against *Pseudomonas aeruginosa* and *Candida albicans* following post-$O_2$ exposure periods up to 48 hours. Kill capacity was measured for both 1 hour and 4 hours exposure periods. The results are presented in Table 10.

TABLE 10

Microbicidal Activity Relative to Period of Air Exposure and Period of Microbial Contact for the Lens Disinfectant-Sterilent Formulations (10 Months After Manufacture)

| Formulation Tested | Time, Post O$_2$ Exposure | Pseudomonas aeruginosa | | Candida albicans | |
|---|---|---|---|---|---|
| | | 1 Hour | 4 Hours | 1 Hour | 4 Hours |
| Control | Immediate | 400,000,000 | 315,200,000 | 5,620,000 | 7,020,000 |
| Control-MPO | Immediate | 344,000,000 | 313,600,000 | 5,860,000 | 7,820,000 |
| Formulation A | Immediate | 0 | 0 | 7,120,000 | 2,760,000 |
| Formulation B | Immediate | 0 | 0 | 2,260,000 | 620,000 |
| Formulation C | Immediate | 0 | 0 | 3,000 | 0 |
| Formulation D | Immediate | 0 | 0 | 0 | 0 |
| Control | 12 Hours | 314,400,000 | 306,400,000 | 4,920,000 | 2,500,000 |
| Control-MPO | 12 Hours | 320,000,000 | 264,000,000 | 5,100,000 | 2,800,000 |
| Formulation A | 12 Hours | 600 | 0 | 132,000 | 1,000 |
| Formulation B | 12 Hours | 600 | 0 | 2,000 | 0 |
| Formulation C | 12 Hours | 0 | 0 | 0 | 0 |
| Formulation D | 12 Hours | 0 | 0 | 0 | 0 |
| Control | 24 Hours | 276,800,000 | 275,200,000 | 5,000,000 | 2,360,000 |
| Control-MPO | 24 Hours | 204,800,000 | 249,600,000 | 5,180,000 | 4,540,000 |
| Formulation A | 24 Hours | 0 | 0 | 0 | 0 |
| Formulation B | 24 Hours | 0 | 0 | 0 | 0 |
| Formulation C | 24 Hours | 0 | 0 | 0 | 0 |
| Formulation D | 24 Hours | 0 | 0 | 0 | 0 |
| Control | 48 Hours | 336,000,000 | 252,000,000 | 1,000,000 | 3,240,000 |
| Control-MPO | 48 Hours | 236,800,000 | 200,800,000 | 3,620,000 | 3,820,000 |
| Formulation A | 48 Hours | 0 | 0 | 0 | 0 |
| Formulation B | 48 Hours | 0 | 0 | 0 | 0 |
| Formulation C | 48 Hours | 0 | 0 | 0 | 0 |
| Formulation D | 48 Hours | 0 | 0 | 0 | 0 |

Eleven months after manufacture, all of the formulations produced total kill of *Pseudomonas aeruginosa* and *Candida albicans* at 24 hours post-O$_2$ exposure times and longer.

Finally, after canister storage for a period of 1 year, the microbicidal activity against *E. coli, P. aeruginosa, C. albicans* and *A. fumigatus* of various dilutions of Formulation D (described above) relative to air exposure times up to 24 hours was determined. The results are shown in Table 11.

As shown in Table 11, after a full year of storage, Formulation D remained highly active against all organisms tested.

While the preferred embodiment of the invention has been illustrated and described, it will be appreciated that various changes can be made therein without departing from the spirit and scope of the invention.

TABLE 11

Microbicidal Activity of Various Dilutions of Formulation D Relative to Air Exposure Time for the Lens Disinfectant-Sterilent Formulations (1 Year After Manufacture)

| Formulation D Dilution Tested | Time Post O$_2$ Exposure | MPO pmol/ml | µg/ml | GOX Units/ml | CFU's after 2 Hours Exposure | | | |
|---|---|---|---|---|---|---|---|---|
| | | | | | E. Coli | P. aeruginosa | C. albicans | Asp. fumigatus |
| Control | Immediate | 0 | 0 | 0 | 280,000,000 | 81,600,000 | 3,340,000 | 2,560,000 |
| Neat | Immediate | 50 | 7 | 2 | 0 | 0 | 0 | 0 |
| 1:2 Dil. | Immediate | 25 | 4 | 0 | 0 | 0 | 1,440,000 | 0 |
| 1:4 Dil. | Immediate | 12 | 2 | 0.5 | 0 | 0 | 3,280,000 | 840,000 |
| 1:8 Dil. | Immediate | 6 | 1 | 0.25 | 99,200,000 | 0 | 1,940,000 | 2,260,000 |
| 1:16 Dil. | Immediate | 3 | 0.5 | 0.12 | 235,200,000 | 90,400,000 | 2,540,000 | 2,460,000 |
| Control | 12 Hours | 0 | 0 | 0 | 212,800,000 | 57,600,000 | 2,520,000 | 5,560,000 |
| Neat | 12 Hours | 50 | 7 | 2 | 0 | 0 | 0 | 0 |
| 1:2 Dil. | 12 Hours | 25 | 4 | 1 | 0 | 0 | 3,200 | 1,600 |
| 1:4 Dil. | 12 Hours | 12 | 2 | 0.5 | 0 | 0 | 3,000,000 | 2,480,000 |
| 1:8 Dil. | 12 Hours | 6 | 1 | 0.25 | 55,200,000 | 0 | 980,000 | 2,920,000 |
| 1:16 Dil. | 12 Hours | 3 | 0.5 | 0.12 | 113,600,000 | 26,400,000 | 2,980,000 | 3,240,000 |
| Control | 24 Hours | 0 | 0 | 0 | 320,000,000 | 63,200,000 | 4,080,000 | 3,600,000 |
| Neat | 24 Hours | 50 | 7 | 2 | 0 | 0 | 0 | 0 |
| 1:2 Dil. | 24 Hours | 25 | 4 | 1 | 0 | 0 | 0 | 0 |
| 1:4 Dil. | 24 Hours | 12 | 2 | 0.5 | 12,000 | 0 | 2,680,000 | 2,400 |
| 1:8 Dil. | 24 Hours | 6 | 1 | 0.25 | 18,000,000 | 0 | 2,500,000 | 1,720,000 |
| 1:16 Dil. | 24 Hours | 3 | 0.5 | 0.12 | 145,600,000 | 17,600 | 2,320,000 | 1,780,000 |

The embodiments of the invention in which an exclusive property or privilege is claimed are defined as follows:

1. A method for killing or inhibiting the growth of microorganisms comprising the steps of:
   (a) maintaining under substantially anaerobic conditions a microbicidal composition comprising a haloperoxidase selected from myeloperoxidase and eosinophil peroxidase, a halide selected from chloride, bromide and combinations thereof, and a peroxide generating agent capable of generating peroxide upon exposure to oxygen;
   (b) exposing the composition to oxygen to activate the microbicidal activity of the composition; and
   (c) contacting the microorganisms with the activated composition to kill or inhibit the growth of the microorganisms.

2. The method in claim 1 wherein the peroxide generating agent is an enzyme capable of oxidizing a substrate and reducing oxygen to hydrogen peroxide.

3. The method of claim 2 wherein the enzyme is glucose oxidase and the substrate is glucose.

4. The method of claim 1 wherein the haloperoxidase is myeloperoxidase.

5. The method of claim 1 wherein the haloperoxidase is eosinophil peroxidase and the halide is selected from the group consisting of bromide, iodide and combinations thereof.

6. The method of claim 1 wherein the microbicidal composition further comprises an antimicrobial activity enhancing agent of the formula:

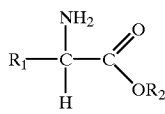

wherein $R_1$ is hydrogen, an unsubstituted, or hydroxy or amino substituted, straight or branched chain alkyl group having from 1 to 6 carbon atoms, and $R_2$ is hydrogen or a straight or branched chain alkyl group having from 1 to 6 carbons.

7. The method of claim 6 wherein the antimicrobial activity enhancing agent is an α-amino acid selected from the group consisting of glycine; the l- or d-enantiomers of alanine, valine, leucine, isoleucine, serine, threonine, lysine, phenylalaninine, and tyrosine; and alkyl esters thereof.

8. The method of claim 1 wherein the microbicidal composition is maintained under anaerobic conditions by packaging the microbicidal composition under pressure in a hermetically sealed container for dispensing as a liquid, a foam or a gel.

9. The method of claim 1 wherein the microbicidal composition is maintained under anaerobic conditions by impregnating the microbicidal composition in a tangible substrate, and then hermetically sealing the impregnated tangible substrate in a closed container.

10. A hermetically sealed container comprising, under substantially anaerobic conditions, an antimicrobial formulation comprising a haloperoxidase selected from myeloperoxidase and eosinophil peroxidase, a halide selected from chloride, bromide and combinations thereof, and a peroxide generating agent capable of generating peroxide upon exposure to oxygen, and means for releasing the formulation from the container.

11. The container of claim 10 wherein the peroxide generating agent is an enzyme capable of oxidizing a substrate and reducing oxygen to hydrogen peroxide.

12. The container of claim 11 wherein the enzyme is glucose oxidase and the substrate is glucose.

13. The container of claim 10 wherein the haloperoxidase is myeloperoxidase.

14. The container of claim 10 wherein the haloperoxidase is eosinophil peroxidase and the halide is bromide.

15. The container of claim 13 which comprises at least 0.01 pmol/ml of myeloperoxidase in a liquid carrier.

16. The container of claim 13 which comprises from 0.1 pmol/ml to 500 pmol/ml of myeloperoxidase.

17. The container of claim 14 which comprises at least 0.01 pmol/ml of eosinophil peroxidase in a liquid carrier.

18. The container of claim 14 which comprises from 0.1 pmol/ml to 500 pmol/ml of eosinophil peroxidase.

19. The container of claim 10 which comprises from 100 nmol/ml to 300 µmol/ml chloride.

20. The container of claim 10 which comprises from 10 nmol/ml to 50 µmol/ml bromide.

21. The container of claim 10 which comprises a peroxide producing oxidase effective to generate from 1 pmol to 50 µmol peroxide per ml per minute when in the presence of a substrate from the oxidase.

22. The container of claim 10 which comprises glucose oxidase effective to generate from 1 pmol to 50 µmol peroxide per ml per minute when in the presence of D-glucose.

* * * * *